United States Patent [19]

Lewellyn et al.

[11] Patent Number: 4,778,921

[45] Date of Patent: Oct. 18, 1988

[54] NOVEL PROCESS OF ALKOXY AND ARYLOXY ISOTHIOCYANATE PREPARATION

[75] Inventors: Morris E. Lewellyn, Fairfield; Samuel S. Wang, New Haven; Peter J. Strydom, Fairfield, all of Conn.

[73] Assignee: American Cyanamid Company, Stamford, Conn.

[21] Appl. No.: 821,302

[22] Filed: Jan. 22, 1986

[51] Int. Cl.$^4$ .................. C07C 125/04; C07C 125/06
[52] U.S. Cl. ..................................... 560/137; 560/148
[58] Field of Search ............................... 560/137, 148

[56] References Cited

PUBLICATIONS

Chem. Ber. 116, 2044, (1983), Goerdeler.

*Primary Examiner*—Alan Siegel
*Attorney, Agent, or Firm*—Frank M. Van Riet

[57] ABSTRACT

Alkoxy and aryloxy isothiocyanates are produced by the reaction of a haloformate and an alkali or alkaline earth metal thiocyanate in the presence of water and a catalyst comprising a six membered mononuclear or ten membered fused polynuclear aromatic, heterocyclic compound having 1 or 2 nitrogen atoms as the only hetero atoms in the ring.

8 Claims, No Drawings

NOVEL PROCESS OF ALKOXY AND ARYLOXY ISOTHIOCYANATE PREPARATION

BACKGROUND OF THE INVENTION

Alkoxy and aryloxy isothiocyanates are well-known versatile, organic intermediates which, by virtue of highly reactive multifunctionalities, can undergo a variety of condensation and cyclization reactions. For instance, Helibron et al, J. Chem. Soc. 1948, 1340, made use of the ready addition of alkoxycarbonyl isothiocyanate to α-aminonitrites in their synthesis related to penicillin and purines. Other useful organic syntheses based on alkoxy and aryloxy isocyanate are set forth by Esmail et al. Synthesis, 301, (1975).

Ethoxycarbonyl isothiocyanate was first prepared by R. E. Doran in 1896 by reacting lead thiocyanate with ethylchloroformate in boiling toluene with relatively poor yields; J. Chem. Soc. 69, 324 (1896). In 1908, Dixon and Taylor reported, J. Chem. Soc. 93, 684 (1908), that methylchloroformate, ethylchloroformate, benzylchloroformate, phenyl chloroformate and o- and p-tolylchloroformate, were reacted with potassium thiocyanate in boiling acetone to form the corresponding isothiocyanate.

One of the reasons for low yields in Dixon et al's method was confirmed by Takamizawa et al to be the simultaneous formation of an unreactive thiocyanate isomer. With ethylchloroformate, two isomers were obtained in about 30% yields while with butylchloroformate the yields were 34% for the isothiocyanate and 21% for the thiocyanate isomer. Yields of 31% for the isothiocyanate and 3.5% for the thiocyanate isomer were obtained with allylchloroformate, it being postulated that the formation of the two isomers were due to the existence of the mesomeric thiocyanate ion and isothiocyanate ion both of which can effect the nucleophilic attack on the carbonyl carbon and cause the thiocyanate and isothiocyanate isomer product. Later workers improved reaction conditions to favor the isothiocyanate formation by adding catalytic amounts of triethylamine and longer reaction times; Goerdeler et al, Chem Ber. 104, 1606 (1971). The use of acetonitrile and ethyl acetate as solvents was reported by Lamon; J. Heterocyclic Chem., 5, 837 (1968); Goerdeler et al; Chem. Ber. 96, 526, (1963). Yields, however, were only up to about 60%. Anders et al, Ger. Pat. No. 1215144, 1966, reported the preparation of alkoxy and aryloxy isothiocyanates using silyl isothiocyanate while Goerdeler et al, Chem. Ber. 98, 2954 (1965) disclosed the pyrolysis of thiozolinediones as a means for producing them, see also Schenk, Chem. Ber. 99, 1258 (1966).

In a later publication, Chem. Ber. 116, 2044, (1983), Goerdeler et al reported the use of an aromatic heterocyclic nitrogen catalyst such as pyridine in carbon tetrachloride for the preparation of alkoxythiocarbonyl isothiocyanate, however, the yield was only 52%. Using the propoxyanalog, Goerdeler et al obtained only a 13% yield of the corresponding isothiocyanate.

The production of phenoxycarbonyl isothiocyanate is also taught by Babu; J. Heterocyclic Chem. 20, 1127, (1983). Thus, the prior art methods for preparing alkoxy and aryloxy isothiocyanates are ineffective in terms of yields and the formation of the undesirable thiocyanate isomer. Additionally, the use of organic solvents creates costly removal problems and poses serious air emission hazards.

SUMMARY OF THE INVENTION

A procedure for the formation of alkoxy and aryloxy isothiocyanates has now been devised whereby the desired products are obtained in higher yields and purity than when prior art techniques are employed. The process of the present invention eliminates the use of organic solvents, and furthermore, since the by-product is alkali metal halide, waste disposal is facilitated.

The process of the present invention resides in the synthesis of the alkoxy and aryloxyisothiocyanates in an all aqueous medium. It was completely unexpected to the instant inventors that such a medium could be employed since both the starting material, i.e., the alkyl or arylhaloformate and product isothiocyanate are normally water-reactive. The use of the aqueous medium is made possible because of the conjoint use therewith of a catalyst comprising six membered mononuclear or ten membered fused polynuclear aromatic, heterocyclic compound having 1 or 2 nitrogen atoms as the only hetero atoms in the ring. The unique combination of catalyst and the aqueous medium unexpectedly allows the isothiocyanate formation in high yields and purity. Furthermore, the product isothiocyanate, a strong lachrymator, although isolatable, need not be so isolated, i.e. it can be reacted in situ with other compounds, e.g. alcohols, amines, mercaptans, etc., to product derivatives, as set forth in copending application, Ser. No. (Case 30,209), filed of even date herewith.

DESCRIPTION OF THE INVENTION INCLUDING PREFERRED EMBODIMENTS

The present invention relates to a process for the production of an alkoxy or aryloxy isothiocyanate which comprises contacting a haloformate having the formula

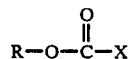

wherein R is a $C_1$–$C_8$ aklyl radical, an alkene radical ($C_2$–$C_4$) or a $C_6$–$C_{10}$ aryl radical and X is a halogen, with an alkali or alkaline earth metal thiocyanate under an appropriate rate of addition of haloformate such as to prevent a run-away reaction, in the presence of water and from about 0.1% to about 10.0% by weight, based on the weight of haloformate, of a catalyst comprising a six membered mononuclear or ten membered fused polynuclear aromatic heterocyclic compound having 1 or 2 nitrogen atoms as the only hetero atoms in the ring and at a temperature ranging from about −10° C. to about 40° C. for up to about 16 hours.

The reaction proceeds according to the equation:

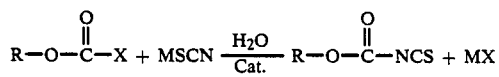

wherein M is an alkali or alkaline earth metal and R and X are as described above.

Both starting materials used in the process of the present invention are well known and any method for their preparation can be used. The alkali or alkaline earth metal thiocyanate may be formed by the reaction of alkali or alkaline earth metal cyanide with sulfur in the presence of a phase transfer catalyst such as a quaternary ammonium salt, see U.S. Pat. No. 4,482,500.

In following the process of the present invention, an equimolar equivalent of the alkoxy or aryloxy haloformate is carefully added to an aqueous solution of the alkali or alkaline earth metal thiocyanate in the presence of the catalyst under the above temperature conditions. A preferred temperature range is 5°–15° C. A preferred catalyst concentration is 0.5 to 5.0%, by weight, based on the weight of haloformate used.

Useful haloformates include the methoxy, ethoxy, isopropoxy, n-butoxy, isobutoxy, amyloxy, hexyloxy, 2-ethylhexyloxy, benzoxy, phenoxy, o- or p-tolyloxy, allyloxy etc, chloro, bromo, iodo, etc., formates.

The catalysts employed in the novel process of the present invention include pyridine, or quinoline, pyrimidine, pyrazine, quinoxaline and the like and substituted derivatives thereof such as their alkyl, halo, nitrile, alkoxy, etc., substituted derivatives. Any derivative may be used except those substituted in the 2-position.

The reaction is conveniently monitored by gas chromatography, whereby samples of the organic layer are periodically withdrawn from the reaction flask and injected into the GC instrument for the disappearance of the haloformate and the appearance of the corresponding isothiocyanate. The reaction time can proceed for up to 16 hours and can vary from one to two hours or eight to ten hours depending on the reaction temperatures, the amount of the catalyst and the concentration of the aqueous alkali or alkaline earth metal thiocyanate. Most haloformates are not water-soluble. The fact that the heterogenous reaction proceeds so well is indeed surprising. The reaction mixture at the end of the reaction is amazingly clean, i.e. the product layer shows very little formation of the thiocyanate isomer. Comparison with a purchased pure isothiocyanate by GC indicate that the crude product is at least 90% pure. The yields are also above 90%. The resultant isothiocyanates can be isolated from the reaction mixture by the addition of sufficient amount of water to dissolve the alkali or alkaline earth metal halide salt and the organic layer separated from the aqueous salt layer by virtue of lower density. Besides GC, the individual isothiocyanate may be characterized by IR, NMR and boiling point. The infrared spectrum of the isothiocyanate includes absorption bands at 1960–1990 cm$^{-1}$ for the N=C=S group, together with peaks at 1750 cm (C=O) and at 1220–1260 cm$^{-1}$ for the C-O group in the alkoxy or aryloxy moiety of the molecule. Boiling points of recovered exemplary isothiocyanates are esentilly the same as those reported in the literature. They are given below:

| PRODUCT | b.p. |
| --- | --- |
| Methoxycarbonyl isothiocyanate | 30° C./12 torr |
| Ethyoxycarbonyl isothiocyanate | 26° C./1.8 torr |
| Butyoxycarbonyl isothiocyanate | 60° C./6 torr |
| Phenyoxycarbonyl isothiocyanate | 87° C./27 torr |

The following examples are set forth for purposes of illustration only and are not to be construed as limitations on the present invention except as set forth in the appended claims. All parts and percentages are by weight unless otherwise specified.

EXAMPLE 1

To 810 parts of an aqueous sodium thiocyanate solution (49.8%) at 0° C. in a suitable reaction vessel with continuous stirring are slowly added 542.5 parts of ethylchloroformate in a thin stream. The temperature rises to 5° C. and is cooled back to −2° C. using an ice/methanol bath. 14.67 Parts of pyridine are added to the reaction medium dropwise over about 10 minutes. The reaction temperature is allowed to slowly rise to 8°–10° C. and the reaction is allowed to proceed until all the ethylchloroformate is reacted, as evidenced by the hourly withdrawal of samples of the organic layer and gas chromatographic (GC) analysis thereof. After about 4 hours, the GC shows essentially no traces of ethylchloroformate and the area percent for ethoxycarbonyl isothiocyanate is nearly 90%. Slight (3%) traces of ethoxycarbonyl thiocyanate are detected. Sufficient water is added to dissolve the sodium chloride by product and the organic layer containing the desired product is recovered.

EXAMPLE 2

The procedure of Example 1 is again followed except that the pyridine is replaced by quinoline. The yield of the pure product is about 90% of theoretical.

EXAMPLE 3

Commercial grade quinoline which contains about 5% isoquinoline is used in place of the pure quinoline of Example 2. Similar results are obtained.

EXAMPLES 4–9

The procedure of Example 1 is again followed except that the catalysts, catalyst concentrations and reaction times and temperatures are varied. The purity of the ethoxycarbonyl isothiocyanate is determined by G.C. and the yields are back calculated based on yields of its alcohol adduct which are known to be near quantitative. The results are set forth in Table 1, below.

TABLE I

| Example | Catalyst (parts/mole) | Time (hrs) | Temp. (°C.) | Purity (%) | Yield (%) |
| --- | --- | --- | --- | --- | --- |
| A* | — | 24 | 25 | 5 | 0 |
| 4 | Pyridine (1.0) | 4.5 | 35 | 85 | 90 |
| 5 | Pyridine (4.5) | 5.5 | 10 | 90 | 95 |
| 6 | Pyridine (3.0) | 7.5 | 10 | 90 | 95 |
| B* | 2-methoxy-pyridine(4.6) | 6.0 | 10 | 4.0 | — |
| 7 | 6-methoxy-quinoline(4.8) | 6.0 | 10 | 95 | 95 |
| 8 | 6-chloro-quinoline(7.1) | 6.0 | 10 | 95 | 93 |
| C* | 2-chloro-pyridine(2.4) | 7 | 10 | 90 | 30 |
| 9 | 4-chloro-pyridine(2.4) | 3 | 10 | 90 | 82 |

*comparative

EXAMPLE 10

The procedure of Example 1 is again followed except that 97.2 parts of potassium thiocyanate solution (50%) and 108.5 parts of ethylchloroformate are used. 4.0 Parts of quinoline are employed and the reaction is conducted at 10° C. for 6 hours. Essentially pure ethoxycarbonyl isothiocyanate is recovered in excellent yield.

EXAMPLE 11

Again following the procedure of Example 1, 81.0 parts of sodium thiocyanate solution (50%) are reacted with 192.5 parts of 2-ethylhexylchloroformate with 4.0 parts of quinoline as the catalyst. The reaction is complete after six hours at 10° C. The resultant 2-ethylhexylcarbonyl isothiocyanate is recovered in high yield.

EXAMPLE 12

Following the procedure of Example 11, n-octylchloroformate is used in place of the 2-ethylhexylchloroformate, all else remaining equal. An excellent yields of n-octylcarbonyl isothiocyanate is recovered.

EXAMPLE 13

Again following the procedure of Example 11 except that ethylbromoformate (152.9 parts) is employed, similar results are achieved.

EXAMPLE 14

To 81 parts of a 50% aqueous sodium thiocyanate solution are added 2.0 parts of quinoline. With stirring, the mixture is cooled to 8° C. with ice/water. Phenylchloroformate (78.3 parts) is introduced dropwise in 1 ½ hours. The reaction is essentially complete in 1 ¾ hours at 10° C., as monitored by GC. The product, phenoxycarbonyl isothiocyanate is recovered as in Example 1 in 85% yield.

EXAMPLE 15

To 81 parts of a 50% aqueous sodium thiocyanate solution are added 2.0 parts of quinoline. The mixture is cooled with stirring to 10° C. with ice/water and 60.3 parts of allylchloroformate are added dropwise over ½ hour. The reaction is monitored by GC and after 2 hours at 10° C. the conversion to allyloxycarbonyl isothiocyanate is only 40%. The temperature is raised to 20° C. and held for an additional two hours after which GC shows substantially complete reaction. Conversion is 89%.

What is claimed is:

1. A process for the production of a alkoxy or aryloxy isothiocyanate which comprises contacting a haloformate having the formula

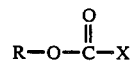

wherein R is an alkyl radical, an alkene radical, or an aryl radical and X is a halogen, with an alkali or alkaline earth metal thiocyanate under an appropriate rate of addition of haloformate such as to prevent a run-away reaction, in the presence of water and from about 0.1% to about 10.0% by weight, based on the weight of haloformate, of a catalyst comprising a pyridine or a quinoline compound unsubstituted in the 2-position and at a temperature ranging from about $-10°$ C. to about 40° C. for up to about 16 hours.

2. A process according to claim 1 wherein R is an ethyl radical.

3. A process according to claim 1 wherein R is a phenyl radical.

4. A process according to claim 1 wherein the haloformate is ethylchloroformate.

5. A process according to claim 1 wherein the alkali metal thiocyanate is sodium thiocyanate.

6. A process according to claim 1 wherein the catalyst is pyridine.

7. A process according to claim 2 wherein the catalyst is quinoline.

8. A process according to claim 1 wherein R is ethyl, X is chlorine, the alkali metal thiocyanate is sodium thiocyanate and the catalyst is quinoline.

* * * * *